United States Patent
Gu

[11] Patent Number: 5,922,768
[45] Date of Patent: Jul. 13, 1999

[54] CARBANILIDE COMPOSITIONS

[75] Inventor: Ben Gu, East Brunswick, N.J.

[73] Assignee: Colgate-Palmolive Co., New York, N.Y.

[21] Appl. No.: 09/071,925

[22] Filed: May 1, 1998

[51] Int. Cl.⁶ ................................................. A61K 31/17
[52] U.S. Cl. .............................................................. 514/596
[58] Field of Search .............................................. 514/596

[56] References Cited

U.S. PATENT DOCUMENTS

| | | | |
|---|---|---|---|
| 2,846,398 | 8/1958 | Beaver et al. | 514/596 |
| 3,177,115 | 4/1965 | Casely et al. | 514/596 |
| 3,594,322 | 7/1971 | Wilson | 514/596 |
| 5,648,328 | 7/1997 | Angell et al. | 510/441 |
| 5,665,742 | 9/1997 | Mori et al. | 514/596 |

FOREIGN PATENT DOCUMENTS

| | | |
|---|---|---|
| 9612468 | 5/1996 | WIPO . |
| 9734988 | 9/1997 | WIPO . |

OTHER PUBLICATIONS

"Poly–Tergent Surfactants, Properties and Applications", 1994, Olin Corporation, 32 pps.
"Poly–G Polyethylene Glycols", 1984, Olin Chemicals, 11 pps.

*Primary Examiner*—James H. Reamer
*Attorney, Agent, or Firm*—Martin B. Barancik

[57] ABSTRACT

A liquid composition comprising
  a) an anti-bacterial aromatic carbanilide
  b) a water soluble polyethylene glycol of molecular weight of at least about 200 the quantity of b sufficient to solubilize the said carbanilide,
  c) a fragrance useful in a personal cleansing composition in quantities sufficient to at least (1) prolong the solubilization of a in b or (2) inhibit the decomposition of the carbanilide or a mixture of (1) and (2).

7 Claims, No Drawings

CARBANILIDE COMPOSITIONS

BACKGROUND OF THE INVENTION

Anti-bacterial agents have been utilized in cleansing compositions for many years. However, in order to utilize an anti-bacterial agent properly, it must be compatible with the composition in which it is present. Various compatibilization methods are known. One of the most difficult materials to properly compatibilize into either a solid or liquid, aqueous formulation is an aromatic carbanilide. Generally, the best known aromatic carbanilide is Trichlorocarbanilide (TCC). This is a well known agent available from Bayer and having a CAS number of 101-20-2. Better dispersion and, therefore, better anti-bacterial efficacy of anti-bacterial agents can be achieved by dissolving such an agent in a solvent prior to mixing in a composition which would be solid when utilized for cleansing purposes. Additionally, such ability to be properly dispersible is also a significant advantage in liquid aqueous formulations as well. A common material utilized for the proper dispersion and/or dissolving of TCC is a polyethylene glycol. However, certain problems occur with such a solubilizing material. Polyethylene glycol is a hydrophilic material. During storage of such a TCC solution, moisture is absorbed from the air. This seems to cause TCC precipitation and/or decomposition. Therefore, a more stable dissolved and/or dispersed composition of TCC is necessary. This will prolong its storage life as well as inhibit decomposition which can lead to the presence of chloroanilines, a material which is undesirable in a cleansing composition.

It has now been found that these solutions of TCC in polyethylene glycol can be further stabilized by the presence of a fragrance which can ordinarily be utilized in a cleansing composition. By incorporating a fragrance into the TCC solution the precipitation of TCC as measured by visual clarity can be extended substantially in some instances more than six months. Additionally, the decomposition of TCC to unwanted chloroanilines is also decreased significantly.

SUMMARY OF THE INVENTION

In accordance with the invention there is a liquid composition comprising:
a) an anti-bacterial aromatic carbanilide,
b) a water soluble polyethylene glycol having a molecular weight of at least about 200, the quantity sufficient to solubilize the said carbanilide of a, and
c) a fragrance useful in a personal cleansing composition in quantities sufficient to at least (1) prolong the solubilization of a in b or (2) inhibit the decomposition of the carbanilide of a when it is solubilized in b, or a mixture of (1) and (2).

Uses of the composition above are in the formulation of various cleansing compositions, both solid and liquid for cleansing the skin upon application and then rinsing with water.

DETAILED DESCRIPTION OF THE INVENTION

The anti-bacterial material which is employed in the invention is an aromatic carbanilide. Specifically and preferably the aromatic carbanilide is halogenated, particularly chlorinated for increased anti-bacterial activity. The preferred aromatic carbanilide is halogenated, particularly chlorinated and is 3,4,4' trichloro carbanilide, known as Triclocarban.

The polyethylene glycol solvent which is used to solubilize the anti-bacterial aromatic carbanilide is water soluble. It has a molecular weight at least about 200. Generally it is lower than about 1000 molecular weight, preferably about 400 to about 800 and more preferably about 500 to about 700.

The TCC or related material is generally solubilized in the polyethlyene glycol by heating the polyethylene glycol to an elevated temperature, at least about 35° C., preferably above about 40° C. and generally, no higher than about 130 to about 140°, preferably no higher than about 95 to 105° C. The anti-bacterial aromatic carbanilide can then be added. If desired the heating can occur after addition of the carbanilide in the polyethylene glycol. When this occurs in appropriate quantities a solubilized aromatic carbanilide is present in the polyethylene glycol. For example, a 20 wt. % TCC solution in polyethylene glycol of molecular weight of about 600 is made by heating at 90° C. The solution is stored in an open or a closed container. However, both of the compositions changed from clear to cloudy in less than 19 hours. This shows that the TCC was precipitating from the composition. Even when polyethylene glycol is heated to an elevated temperature prior to addition of TCC in order to remove absorbed moisture, the TCC is still precipitated out. For example, an aged polyethylene glycol of molecular weight of about 600 is heated to 115° C. to remove absorbed moisture. 20 wt. % TCC is solubilized in the polyethylene glycol at 90° C. The solution is aged in open and closed containers. Although the cloudiness was delayed to the sixth day of aging, it is still observed at that time. Therefore, it is clear from these results that stabilization of a polyethylene glycol solution of TCC, particularly in a reasonable temperature range, would be a significant advantage for maintaining storage of these materials.

It has now been found that the presence of a fragrance in the aromatic carbanilide anti-bacterial agent solubilized in the polyethylene glycol composition brings about an increased stability as measured by visual clarity, indicating the presence of precipitated material. It also has been shown that the presence of the fragrance inhibits the decomposition of such materials, particularly the halogenated, i.e chlorinated antibacterial materials to decomposition products such as chloroanilines.

By fragrance is meant any volatile perfume agent which provides an odor to the final composition in which the fragrance residues. Examples of such materials are those boiling at temperatures below about 500° C. The highly volatile, low boiling, perfume ingredients typically have boiling points of about 250° C. or lower. The moderately volatile perfume ingredients are those having boiling points of from about 250° C. to about 300° C. The less volatile, high boiling perfume ingredients are those having boiling points of about 300° C. to about 500° C. Many of the perfume ingredients as discussed hereinafter along with their odor and/or flavor characters, and their physical and chemical properties, such as boiling point and molecular weights are given in "Perfume and Flavor Chemicals (Aroma Chemicals)," Steffen Arctander, published by the author, 1969, incorporated herein by reference. It is preferred that the personal cleansing products herein contain a fragrance having at least about 5% of its components, more preferably at least about 25%, and most preferably at least about 50% of the fragrance components as highly volatile perfume ingredients having a boiling point of 250° C. or lower.

Examples of the highly volatile, low boiling perfume ingredients are: anethole, benzaldehyde, benzyl acetate, benzyl alcohol, benzyl formate iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate and vertenex (para-tertiary-butyl cyclohexyl acetate). Some natural oils also contain large percentages of highly volatile perfume ingredients. For example, lavandin contains as major components: linalool; linalyl acetate; geraniol and citronellol. Lemon oil and orange terpenes both contain about 95% of d limonene. Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

Examples of the less volatile, higher boiling perfume ingredients are: benzophenone, benzyl salicylate, ethylene brassylate, galaxolide (1,3,4,6,7,8-hexahydro-4,6,6,7,8,8-hexamethyl-cyclopenta-gama-2-benzopyran), hexyl cinnamic aldehyde, lyral (4-(4-hydroxy-4-methyl pentyl)-3-cyclohexene-10-carboxaldehyde), methyl cedrylone, methyl dihydro jasmonate, methyl-beta-naphthyl ketone, musk indanone, musk ketone, musk tibetene, and phenylethyl phenyl acetate.

The fragrance should be present in quantities sufficient to at least (1) prolong the solubilization of a in b or (2) inhibit the decomposition of the anti-bacterial aromatic carbanilide or a mixture of (1) and (2). Generally, these quantities are not very high and are at least 0.01 and can be from about 0.01 to about 5.0 wt. % of the polyethylene glycol solubilized aromatic carbanilide solution, preferably from about 0.15 to about 4 wt. %. Lower maximum quantities of fragrance can be used if desired for example about 3, 2 or 1 wt. %. If possible, the weight percents of the fragrance are related to the final cleansing composition in which the anti-bacterial aromatic carbanilide is present. Generally these are from about 0.01 to about 5 wt. % of the composition, preferably from about 0.1 to about 2.0 wt. %. In this manner, the final composition need not have any more fragrance added to it than is necessary for its intended purpose. However, additional fragrance can certainly be added to the final composition if required.

Such cleansing compositions are those generally known in the art. They can be either solid materials such as hand held bars for personal cleansing or aqueous formulations having either soap or other surfactants therein. Cleansing composition for surfaces other than skin, particularly kitchen counters, floors, bathrooms fixtures and the like are also contemplated and within the invention.

These cleansing compositions have one or more surfactants therein. The surfactants which can be added include the following Soap, a long chain alkyl or alkenyl, branched or normal carboxylic acid salt such as sodium, potassium, ammonium or substituted ammonium salt, can be present in the composition. Exemplary of long chain alkyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like.

Other surfactants can be present in the composition as well. Examples of such surfactants are the anionic, amphoteric, nonionic and cationic surfactants. Examples of anionic surfactants include but are not limited to alkyl sulfates, acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Alkyl chains for these surfactants are $C_8$–$C_{22}$, preferably $C_{10}$–$C_{18}$, more preferably $C_{12}$–$C_{14}$.

Anionic nonsoap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol e.g., tallow or coconut oil alcohols and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

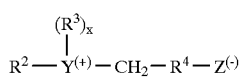

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate and phosphate groups.

Examples include: 4-[N,N-di(2-hydroxyethyl)-N-octadecylammonio]-butane-1- carboxylate; 5-[S-3- hydroxypropyl-S-hexadecylsulfonio]-3-hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio-propane-1-phosphonate; 3-(N,N-di-methyl-N-hexadecylammonio) propane-1-sulfonate; 3-(N,N-dimethyl-N- hexadecylammonio)-2-hydroxypropane-1-sulfonate; 4-(N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)- propane-1-phosphonate; and 5-[N,N-di(3-hydroxypropyl)-N-hexadecylammonio]-2- hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438, 091, and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2- hydroxyethyl)carboxy methyl betaine, stearyl bis-(2-hydroxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:
stearyldimenthylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride
laurylpyridinium chloride;
laurylisoquinolium bromide;
ditallow(Hydrogenated)dimethyl ammonium chloride;
dilauryldimethyl ammonium chloride; and
stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

$$R_1R_2R_3N \longrightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2- dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2- hydroxypropyldi(2-hydroxyethyl) phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

7. Alkylated polyglycosides wherein the alkyl group is from about 8 to about 20 carbon atoms, preferably about 10 to about 18 carbon atoms and the degree of polymerization of the glycoside is from about 1 to about 3, preferably about 1.3 to about 2.0.

However any one of these families of surfactants or various combinations need not be present in the final cleansing composition. Anionic surfactants are preferred.

The liquid and solid cleaning compositions are prepared by standard methods. The solubilized TCC is added at the normal place in the sequence of steps.

Other components may be present in the composition, for example colorant, preservatives, pearlescents, moisturizing aids, emollients, occlusive agent, and the like. However, any one or various combinations of these materials need not be present in the final cleansing formulation.

Below are examples of the invention. These examples are intended to illustrate the broad inventive nature of the invention and are not intended to unduly narrow this inventive concept.

EXAMPLES

Comparison Example 1

A 20 wt. % TCC solution in polyethylene glycol of molecular weight of about 600 is made by heating the two components at 90° C. The solution is divided and stored in open and closed containers. As aforementioned earlier, these compositions change from clear to cloudy in less than 19 hours.

Example 1

The same TCC solution in polyethylene glycol as in Comparison Example 1 is prepared at 90° C. This solution is mixed with Sandia fragrance at 25° C. at a weight ratio of 1 to 1, the final composition being 50% fragrance and 50 wt. % of the 20 wt. % TCC solution in polyethylene glycol. Major components of the Sandia fragrance include benzyl alcohol, amyl salicylate, benzyl salicylate and phenyl ethyl alcohol. This mixture is aged at room temperature for more than 6 months. It remains clear.

Example 2

A TCC composition is prepared by mixing 0.3 parts by weight of TCC, 1.2 parts by weight polyethyleneglycol of molecular weight 600, and 1 part by weight Sandia fragrance. The composition is 12% by weight TCC, 48% by weight polyethylene glycol, and 40% by weight Sandia fragrance. Starting at 25° C., the temperature is raised until a clear solution is achieved at 45° C. The solution remains clear in an open container for 4 days and turns cloudy on the fifth day. This shows the influence of temperature of mixing on the stability of the final composition.

This composition is particularly useful since a soap bar having 97.5% soap base and 2.5 wt. % of this composition has a TCC level of 0.3 wt. % and a Sandia fragrance level of 1 wt. %.

Example 3

A 20 wt. % trichlocarban solution in polyethylene glycol of molecular weight of about 600 is prepared at 90° C. The preparation is divided in half and cooled to room temperature. The first half is aged for 15 days and the chloroaniline level measured. To the second half of the mixture is added Sandia fragrance at 25° C. to give a final weight ratio of 50 wt. % mixture and 50 wt. % Sandia fragrance. After 15 days, the chloroaniline level is measured. Below are the results:

| Solution | Chloroaniline level, ppm |
| --- | --- |
| 20 wt. % TCC in PEG | 232 |
| 20 wt. % TCC in PEG, 50 wt. % - Fragrance, 50 wt. % | 58 |

From this data, it is clear that the presence of fragrance clearly inhibits the degradation of the aromatic carbanilide.

I claim:

1. A liquid composition comprising a) an anti-bacterial aromatic carbanilide b) a water soluble polyethylene glycol of molecular weight of at least about 200 the quantity of b sufficient to solubilize the said carbanilide, c) a fragrance useful in a personal cleansing composition in quantities sufficient to at least (1) prolong the solubilization of a in b or (2) inhibit the decomposition of the carbanilide or a mixture of (1) and (2).

2. A process for stabilizing an anti-bacterial aromatic carbanilide solubilized in water soluble polyethylene glycol of molecular weight of at least about 200 which comprises contacting together the anti-bacterial aromatic carbanilide, the said polyethylene glycol and a fragrance.

3. The composition in accordance with claim 1 wherein the molecular weight of the polyethylene glycol is below about 1000.

4. The composition in accordance with claim 1 wherein the carbanilide is triclocarban.

5. The composition in accordance with claim 4 wherein the molecular weight of the polyethylene glycol is below about 1000.

6. The process in accordance with claim 2 wherein the carbanilide is triclocarban.

7. The process in accordance with claim 6 wherein the polyethylene glycol and triclocarban are contacted at a temperature above about 35° C.

* * * * *